United States Patent
Rieger

(10) Patent No.: US 10,716,807 B2
(45) Date of Patent: Jul. 21, 2020

(54) METHOD OF TREATING RELAPSING-REMITTING MULTIPLE SCLEROSIS USING ARSENIC TRIOXIDE

(71) Applicant: Medsenic, Strasbourg (FR)

(72) Inventor: François Rieger, Geneva (CH)

(73) Assignee: MEDSENIC, Strasbourg (FR)

(*) Notice: Subject to any disclaimer, the term of this patent is extended or adjusted under 35 U.S.C. 154(b) by 0 days.

(21) Appl. No.: 15/590,254

(22) Filed: May 9, 2017

(65) Prior Publication Data
US 2018/0325944 A1    Nov. 15, 2018

(51) Int. Cl.
*A61K 33/36* (2006.01)
*A61P 25/00* (2006.01)
*A61P 37/00* (2006.01)

(52) U.S. Cl.
CPC ............. *A61K 33/36* (2013.01); *A61P 25/00* (2018.01); *A61P 37/00* (2018.01)

(58) Field of Classification Search
CPC ..................................................... A61K 33/36
See application file for complete search history.

(56) References Cited

U.S. PATENT DOCUMENTS

| | | | |
|---|---|---|---|
| 2004/0110691 A1* | 6/2004 | Stamler | A61K 31/12 514/1.2 |
| 2008/0193560 A1* | 8/2008 | Hwang | A61K 45/06 424/623 |
| 2010/0040537 A1* | 2/2010 | Gu | C07K 16/26 424/1.11 |
| 2016/0220627 A1* | 8/2016 | Melnick | A61K 31/11 |

FOREIGN PATENT DOCUMENTS

WO    WO-2014045083 A1 *  3/2014

OTHER PUBLICATIONS

Woo et al. ("Mitoxantrone-Associated Leukemia in Multiple Sclerosis: Case Studies", Int J MS Care. 2008;10:41-46).*

* cited by examiner

*Primary Examiner* — Robert A Wax
*Assistant Examiner* — Quanglong N Truong
(74) *Attorney, Agent, or Firm* — Arrigo, Lee, Guttman & Mouta-Bellum LLP

(57) ABSTRACT

The present invention relates to a method for preventing or treating multiple sclerosis, particularly relapsing-remitting multiple sclerosis using arsenic trioxide.

5 Claims, 3 Drawing Sheets

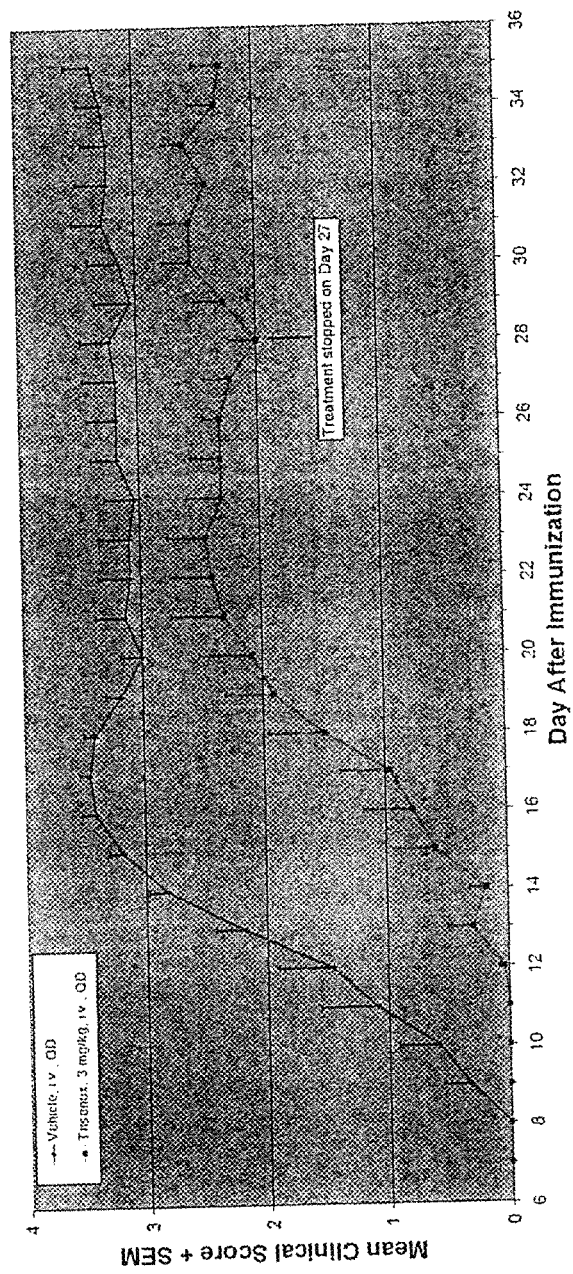
Figure 1 - EAE severity (mean clinical score) vs. time

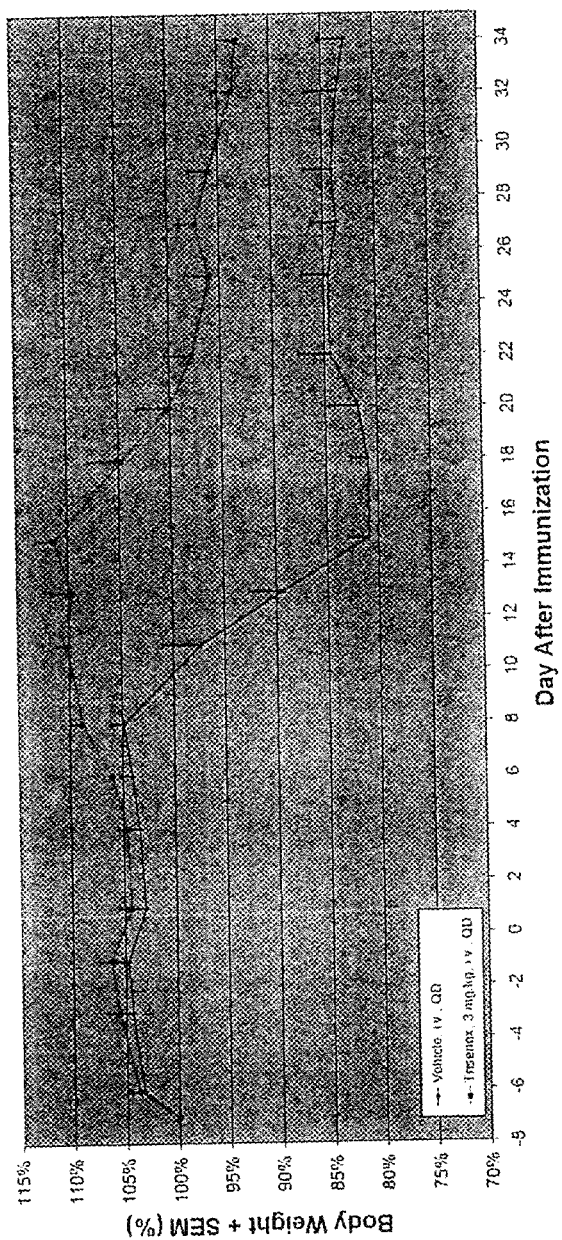
Figure 2 - Change in body weight vs. time

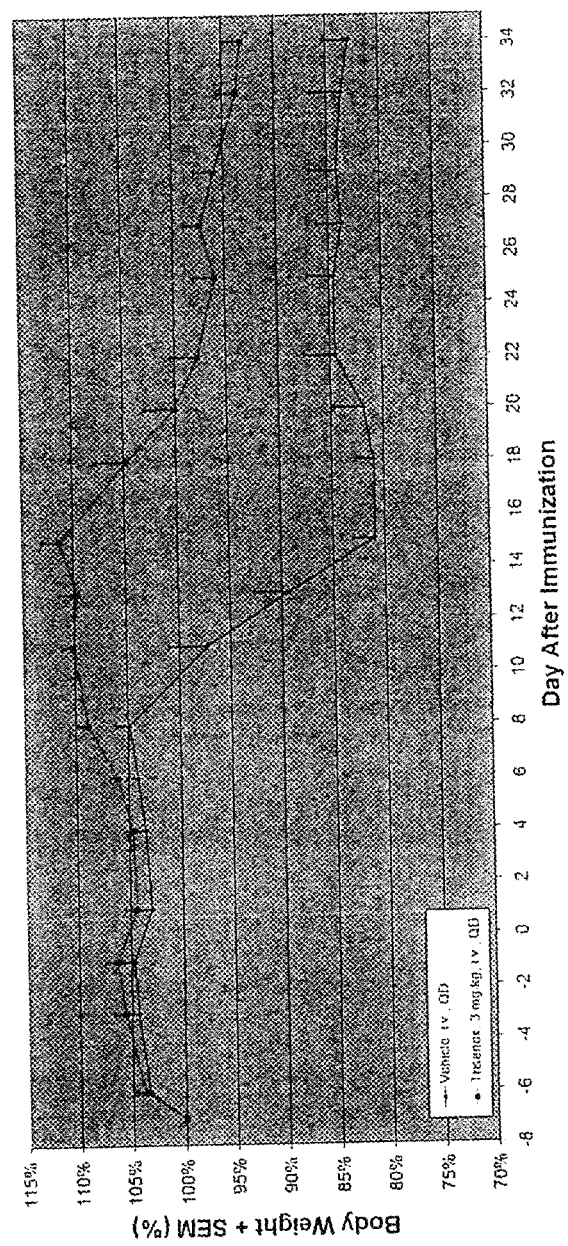
Figure 3 – IL-6 concentration in spleen cultures

METHOD OF TREATING RELAPSING-REMITTING MULTIPLE SCLEROSIS USING ARSENIC TRIOXIDE

FIELD OF THE INVENTION

The present invention relates to a method for treating and/or preventing multiple sclerosis, in particular relapsing-remitting multiple sclerosis.

BACKGROUND

Multiple sclerosis (MS), also known as disseminated sclerosis or encephalomyelitis disseminata, is a demyelinating disease in which the insulating covers of nerve cells in the brain and spinal cord are damaged. This damage disrupts the ability of parts of the nervous system to communicate, resulting in a wide range of signs and symptoms, including physical, mental, and sometimes psychiatric problems.

MS takes several forms, with new symptoms either occurring in isolated attacks (relapsing forms) or building up over time (progressive forms). Between attacks, symptoms may disappear completely; however, permanent neurological problems often occur, especially as the disease advances.

MS is the most common autoimmune disorder affecting the central nervous system.

To date, there is no known cure or prophylactic treatment for MS. Treatments attempt to improve function after an attack and prevent new attacks. Medications used to treat MS, while modestly effective, can have adverse effects and be poorly tolerated. Corticosteroids, such as oral prednisone and intravenous methylprednisolone, are prescribed to reduce nerve inflammation. Other treatments for relapsing-remitting MS include beta interferons, glatiramer acetate (Copaxone), Dimethyl fumarate (Tecfidera), fingolimod (Gilenya), teriflunomide (Aubagio), natalizumab (Tysabri), alemtuzumab (Lemtrada) and mitoxantrone. Many people pursue alternative treatments, despite a lack of evidence.

During the 2000s and 2010s, several oral drugs have been approved. Other oral drugs are under investigation, including ozanimod and laquinimod. Laquinimod was announced in August 2012 and is in a third phase III trial after mixed results in the previous ones. Similarly, studies aimed to improve the efficacy and ease of use of already existing therapies are being carried out. This includes the use of new preparations or derivatives of known drugs such as the PEGylated version of interferon-β-1a.

Monoclonal antibodies have also raised interest. Alemtuzumab, daclizumab, and CD20 monoclonal antibodies such as rituximab, ocrelizumab, ofatumumab or anti HERV W Env are thought to be of some benefit and are under study as potential treatments. Their use has often been accompanied by the appearance of potentially dangerous adverse effects, the most important of which being opportunistic infections.

Another research strategy is to evaluate the combined effectiveness of two or more drugs. The main rationale for using a number of medications in MS is that the involved treatments target different mechanisms and, therefore, their use is not necessarily exclusive. Synergies are also possible, but there can also be drawbacks such as the blocking of the action of the partner medication or worsened side-effects.

There is still an unmet need in the art for prophylactic or therapeutic agents able to prevent, delay the onset and/or treat multiple sclerosis, in particular relapsing-remitting multiple sclerosis (RRMS). All treatment options are of potential great value for MS: prophylactic (before onset of symptoms), semi-therapeutic (at the start of the clinically defined disease) or therapeutic (during the course of the disease). Since there is no known marker for the sub-clinical manifestations of the disease (before the onset of the recognized symptoms, often visual manifestations) all treatment regimens likely to be adopted will be of therapeutic nature, destined at decreasing the intensity of the disease or delaying its time course or clinical evolution.

Fowler's solution is a solution containing 1% potassium arsenite ($KAsO_2$), and was once prescribed as a remedy or a tonic. From 1845, Fowler's solution was used as a leukemia treatment.

As some arsenical compounds are notably toxic and carcinogenic, with side effects such as cirrhosis of the liver, idiopathic portal hypertension, urinary bladder cancer, and skin cancers, Fowler's solution fell from use.

Interest in arsenic compounds returned with the use of Arsenic Trioxide ($As_2O_3$) as an anti-cancer ("antineoplastic" or "cytotoxic") chemotherapy. It has been approved by the US FDA for the treatment of acute promyelocytic leukemia that is unresponsive to "first line" agents, namely all-trans retinoic acid (ATRA). It has been shown that arsenic trioxide induces cancer cells to undergo apoptosis. The combination therapy of arsenic trioxide and all-trans retinoic acid (ATRA) has been approved by the U.S. Food and Drug Administration (FDA) for the treatment of acute promyelocytic leukemia.

Bobé et al. (Blood, 108, 13, p 3967-3975, 2006) investigated the effects of arsenic trioxide in a mouse model of systemic lupus erythematosus. $As_2O_3$ significantly prolonged survival of MRL/lpr mice by preventing young mice from developing the syndrome and quasi-totally reversing established disease in older animals. These authors suggested that this compound might be useful in the treatment of autoimmune diseases such as lupus erythematosus.

However, it has not yet been demonstrated that arsenic trioxide could be used in the treatment or prevention of multiple sclerosis, which is a specific autoimmune disease targeting the central nervous system.

SUMMARY

The inventors have shown that arsenic trioxide could be used in the treatment and the prevention of multiple sclerosis. More specifically, they have shown in a well-known and recognized mouse model of MS demonstrating inflammatory features reminiscent of the human RRMS, that arsenic trioxide could be used to prevent, delay the onset and/or treat the inflammatory phase characterizing the RRMS form of MS.

Thus, the present invention relates to a method for preventing, delaying the onset or and/or treating multiple sclerosis in a patient, comprising the step of administering a therapeutically effective amount of arsenic trioxide to said patient.

DETAILED DESCRIPTION

The present invention relates to a method for preventing, delaying the onset and/or treating multiple sclerosis in a patient comprising the step of administering a therapeutically effective amount of arsenic trioxide to said patient.

In a particular embodiment, the present invention relates to a method for preventing, delaying the onset and/or treating relapsing-remitting multiple sclerosis (RRMS) in an affected individual, comprising the step of administering a therapeutically effective amount of arsenic trioxide to said individual.

As used herein, the term "treat" or "treating" and their derivatives includes substantially inhibiting, slowing or reversing the progression of a condition, substantially ameliorating symptoms of a condition or substantially preventing the appearance of symptoms of a condition.

The term "prevent" and all variations of this term is intended to mean the countering in advance of multiple sclerosis symptoms. In this case it is understood that the composition is applied prior to the observation of the first symptoms.

The terms "ameliorate" and "amelioration" relate to the improvement in the treated subject's condition brought about by the compositions and methods according to the invention.

The expression "delaying the onset" is interpreted as preventing or slowing the progression of multiple sclerosis, such that certain symptoms of MS appear later than in the absence of the treatment according to the invention.

"Relapsing-remitting multiple sclerosis" or "RRMS" is characterized by clearly defined attacks of new or increasing neurologic symptoms. These attacks—also called relapses or exacerbations—are followed by periods of partial or complete recovery (remissions). During remissions, all symptoms may disappear, or some symptoms may continue and become permanent. However, there is no apparent progression of the disease during the periods of remission.

At different points in time, RRMS can be further characterized as either active (with relapses and/or evidence of new MRI activity) or not active, as well as worsening (a confirmed increase in disability over a specified period of time following a relapse) or not worsening. An increase in disability is confirmed when the person exhibits the same level of disability at the next scheduled neurological evaluation, typically 6 to 12 months later.

Without wishing to be bound by theory, it is considered that the pathological mechanisms underlying relapsing-remitting forms of MS are unique and different from those of other autoimmune diseases, such as lupus erythematosus or Graft-versus-Host disease.

The first point is that each disease targets different antigens/cells/organs with very different clinical manifestations. MS is in particular considered as specifically attacking the central nervous system, at the exclusion of other organs. The production of autoantibodies is known to involve specific antigens of the central nervous system, mainly MBP, PLP and other myelin components, which relates to the main physiological disturbance of the disease, namely nerve conduction defects in the central nervous system including the optic nerve.

Recent advances in genome-wide association studies (GWAS) across autoimmune and immune-mediated diseases have augmented our understanding of pathogenic mechanisms underlying these diseases. This has further highlighted their heterogeneous nature, both within and between diseases. Furthermore, varying responses to therapy have also served to underline the importance of this heterogeneity in the manner in which these diseases are diagnosed and treated». Cho and Feldman 2015 have discussed «the current understanding of the shared pathways of autoimmunity, including the tumor necrosis factor (TNF), major histocompatibility complex (MHC), interleukin 23 receptor (IL23R) and protein tyrosine phosphatase non-receptor type 22 (PTPN22) pathways.» In addition, effective specific therapies tested across major autoimmune diseases, highlight «the insight they have provided into disease mechanisms and their implications for potential future improvements».

According to one aspect, the invention relates to a pharmaceutical composition intended for the treatment and/or prevention of multiple sclerosis, particularly RRMS, characterized in that it comprises an effective amount of arsenic trioxide. This effective amount intended to be administered daily is a dose of 0.01 to 5 mg/kg of bodyweight, preferably 0.05 to 0.5 mg/kg, even more preferably 0.10 to 0.30 mg/kg.

This composition may also comprise a pharmaceutically acceptable carrier or excipient. Depending on the applications, it will be in a form that is suitable for any appropriate route of administration, e.g., oral, dermal, parenteral, intraperitoneal administration.

The carrier may be of very varied type, according to the form of the preparation used for the administration, in particular oral, dermal or parenteral (lozenge, capsule, powder, intravenous liquid or encapsulated injection, infusion or ingestion).

For oral administration, the pharmaceutical preparation may be preferably but not only in liquid form, for example in solution, in the form of a syrup or of a suspension, or in the form of a powder intended to be re-dissolved. Such a liquid preparation can be prepared according to suitable techniques with pharmaceutically acceptable excipients such as suspending agents (for example: sorbitol, cellulose derivatives), emulsifiers (for example: lecithin or acacia), non-aqueous transporters (for example: fractionated vegetable oil), and preserving agents (for example: sorbic acid).

When solid oral preparations (lozenge, powder, capsule, tablet) are involved, the pharmaceutical compositions are prepared using suitable excipients such as binding agents (corn starch, polyvinyl pyrrolidone, hydroxypropylmethylcellulose), filling agents (lactose, microcrystalline cellulose), lubricants (magnesium stearate, talc, silica) or swelling agents (sodium lauryl sulfate).

In one embodiment, the arsenic trioxide is not in the form of Fowler's solution.

In one embodiment, the arsenic trioxide is not associated with neoarsphenamine.

In one embodiment, the arsenic trioxide is not administered by oral administration.

For administration by inhalation, the compounds are typically included in a preparation of the aerosol type using a suitable gas.

The arsenic trioxide can also be formulated for parenteral administration, for example by continuous or non-continuous injection. The liquid media are generally similar (water, glycol, oil, buffer) to those used for oral preparations.

The formulations by injection can be provided in the form of dosage units (ampoules, mini-containers) with a suitable protective agent. These compositions to be injected can also be in the form of a suspension, a solution or an emulsion and can contain stabilizers and/or dispersing agents. The active principle can also be prepared in the form of a powder with a suitable transporter or encapsulated or incorporated in a suitable transdermal preparation or patch. The invention also provides packs or kits comprising at least one container containing the arsenic trioxide in a pharmaceutically acceptable form. For example, the arsenic trioxide may be in the form of a pharmaceutically acceptable solution, such as a saline solution, a dextrose solution or a sterile buffer solution; the kit may also comprise suitable means for injection, such as a sterile packaged syringe.

The therapeutic dose used in the treatment of multiple sclerosis is variable according to the seriousness and the conditions of treatment. The dose, and where appropriate the frequency, are to be adjusted as a function in particular of age and of bodyweight, in addition to severity of disease and its stage. Given the potential toxicity of the arsenic, the dosage and the duration of the treatment are determined in an appropriate manner, according to the seriousness of the disease and the long-lasting nature, or otherwise, of the recovery, it being possible for the treatment to last from a few days to a few months until complete or at least partial recovery is achieved. The formulation is typically administered daily, for a period of 10 to 50 days. Several successive treatments may be carried out, of the order of one month apart.

In addition, the arsenic trioxide may be administered, where appropriate, with other active principles that participate in the treatment of the targeted diseases. Thus, mention may be made of the use of the arsenic in combination with corticosteroids such as prednisone or drugs such as methotrexate, for treating autoimmune syndromes and/or chronic inflammatory pathologies or any other active component which may occur to add or synergize to the prophylactic, therapeutic or curative action of arsenic salts.

According to another aspect, the invention relates to a method for treating, in particular in humans, multiple sclerosis comprising the administration to the patient of a pharmaceutically effective amount of arsenic trioxide. The invention relates to a method of treatment comprising the administration of 0.01 to 5 mg, preferably 0.05 to 0.5 mg, even more preferably 0.10 to 0.30 mg of arsenic trioxide per kilogram of bodyweight per day. The administration may be oral, transdermal, parenteral, intraperitoneal, intravenous or via any other appropriate route.

In one embodiment of the invention, the patient does not suffer from cancer, in particular acute promyelocytic leukemia.

Other subjects and advantages of the invention will emerge on reading the detailed description illustrated by means of the drawings in which:

FIG. 1 shows EAE severity (mean clinical score) vs time.

FIG. 2 shows change in body weight vs time.

FIG. 3 shows IL-6 concentration (average of triplicates) in spleen cultures after 72 hours of incubation with various concentrations of MOG35-55 (0, 0.7, 2.2, 6.7 and 20.0 µg/mL).

EXAMPLES

Example 1

Summary

The study objective was to evaluate the effects of arsenic trioxide (1 mg/ml), administered i.v., QD, starting 7 days before EAE induction, on EAE development in the MOG35-55-induced prophylactic/therapeutic EAE model, known as the more robust and direct animal model to trigger and observe the autoimmune cascade involving the central nervous system and ensuing demyelination.

The inventors' goal was to verify the compound efficacy on the inflammatory processes active in early MS development (RRMS), thus focusing on the early manifestations of the RRMS form of the disease, since the progressive form is now thought to involve neurodegenerative mechanisms more than inflammatory or strictly autoimmune mechanisms.

EAE was induced by MOG35-55/CFA immunization and pertussis toxin injection in C57BL/6 mice.

There were 2 experimental groups with 12 mice per group. Mice were treated prophylactically.

Arsenic trioxide was efficacious at postponing EAE onset and reducing disease severity in this study. In addition, the efficacy was maintained 7 days after the treatment was stopped.

Material and Methods

Model Background

Experimental autoimmune encephalomyelitis (EAE) is the most commonly used mouse model of human multiple sclerosis (MS). Because of its many similarities to MS, EAE is used to study pathogenesis of autoimmunity, CNS inflammation, demyelination, cell trafficking and tolerance induction.

EAE is characterized by paralysis, CNS inflammation and demyelination. EAE is mediated by myelin-specific CD4+ T cells, but CD8+ cells and B cells may also play a role in some models of EAE.

EAE is induced in C57BL/6 mice by immunization with MOG35-55 or MOG1-125 in CFA emulsion followed by administration of PTX in PBS. The emulsion provides antigen which initiates expansion and differentiation of MOG-specific autoimmune T cells.

PTX enhances EAE development by providing additional adjuvant and facilitating entrance of autoimmune T cells into the CNS.

FTY720 is the most commonly used positive control in this model.

Chronic EAE develops in C57BL/6 mice after immunization with an emulsion of MOG35-55/CFA or MOG1-125/CFA followed by injection of pertussis toxin. This model is used to test the potential of compounds to prevent or mitigate EAE disease. It can be run with the compound dosed from the time of immunization (prophylactic treatment), or with the aim of reversing the course of disease and facilitating recovery by dosing the compound from the time of EAE onset (therapeutic treatment).

The MOG1-125 antigen is used for testing therapeutics which specifically target B-cells; EAE development after immunization with MOG1-125 is reported to be impaired in B-cell deficient mice.

The model uses female C57BL/6 mice of age 10 to 14 weeks at the start of the study. Typically, EAE develops 8 to 18 days after immunization. EAE development is usually followed for 4 weeks (28 days) after immunization.

Stress reduces mouse susceptibility to EAE. Aside from any compound effects, the administration of treatment during the disease induction period (~0-10 days after immunization) postpones disease onset and reduces disease severity. This is due to the stress of compound administration and the effects of the vehicle on the mice. The more frequent the administration and the less tolerated the vehicle, the greater the impact on disease development.

The stress of treatment and administration of vehicle has less effect on disease development after clinical signs of EAE have appeared.

EAE Induction

Mice were acclimated to our facility for 1 week prior to the start of the study.

The study used a total of 24 female C57BL/6 mice (Taconic Farms, 10 weeks old).

EAE was induced in all mice as follows:
Day 0, Hour 0—Immunization with $MOG_{35-55}$/CFA
Day 0, Hour 2—Injection of pertussis toxin
Day 1, Hour 0—$2^{nd}$ injection of pertussis toxin (24 hours after initial immunization)

Mice were injected subcutaneously at two sites in the back with the emulsion component (containing $MOG_{35-55}$) of Hooke Kit™ $MOG_{1-125}$/CFA Emulsion PTX, catalog number EK-2110 (Hooke Laboratories, Lawrence Mass.). One site of injection was in the area of upper back, approximately 1 cm caudal of the neck line. The second site was in the area of lower back, approximately 2 cm cranial of the base of the tail. The injection volume was 0.1 mL at each site.

Within 2 hours of the injection of emulsion, and then again 24 hours after the injection of emulsion, the pertussis toxin component of the kit was administered intraperitoneally. The volume of each injection was 0.1 mL.

To optimize disease severity for this particular study, the pertussis toxin was administered at 165 ng/dose for the first injection and 154 ng/dose for the second injection.

Groups and Treatment

There were 2 groups of 12 mice each.

Mice were assigned to groups 7 days before immunization (Day −7), balanced to achieve similar weight at the start of the study.

Treatment was according to Table 1 below.

TABLE 1

Groups and treatment

| Group | Treatment | Route | Dose | Volume | Freq. | Purpose |
|---|---|---|---|---|---|---|
| 1 | Vehicle | i.v. | — | 10 mL/kg | QD | Negative control |
| 2 | arsenic trioxide | i.v. | To Day −1: 2 mg/kg To Day 27: 3 mg/kg | 10 mL/kg | QD | Test compound |

Dosing of all mice was at the same time (+/−1 hour) on each day.

Dosing of all mice started on Day −7 (7 days before EAE induction) and continued until Day 27.

Group 2 was dosed at 2 mg/kg from Day −7 to Day −1, and at 3 mg/kg until Day 27.

Mice were scored for EAE and weighed until Day 35, the last day of the study.

Scoring and Readout

Readouts were EAE scores and body weight at the end of the study.

Mice were scored daily from Day 7 after immunization until the end of the study, and body weight was measured three times/week (Monday, Wednesday and Friday), starting on Day −7.

Scoring was performed blind, by a person unaware of both treatment and of previous scores for each mouse.

EAE Scoring

EAE was scored on scale 0 to 5:

0 No obvious changes in motor functions of the mouse in comparison to non-immunized mice.
  When picked up by the tail, the tail has tension and is erect. Hind legs are usually spread apart. When the mouse is walking, there is no gait or head tilting.

1 Limp tail.
  When the mouse is picked up by the tail, instead of being erect, the whole tail drapes over finger.

2 Limp tail and weakness of hind legs.
  When mouse is picked up by tail, legs are not spread apart, but held closer together. When the mouse is observed walking, it has a clearly apparent wobbly walk.

3 Limp tail and complete paralysis of hind legs (most common).
  OR
  Limp tail with paralysis of one front and one hind leg.
  OR
  ALL of:
    Severe head tilting,
    Walking only along the edges of the cage,
    Pushing against the cage wall,
    Spinning when picked up by the tail.

4 Limp tail, complete hind leg and partial front leg paralysis.
  Mouse is minimally moving around the cage but appears alert and feeding.
  Usually, euthanasia is recommended after the mouse scores level 4 for 2 days. When the mouse is euthanized because of severe paralysis, score of 5 is entered for that mouse for the rest of the experiment.

5 Complete hind and complete front leg paralysis, no movement around the cage.
  OR
  Mouse is spontaneously rolling in the cage.
  OR
  Mouse is found dead due to paralysis.

In-between scores were assigned when the clinical signs fell between two above defined scores.

Statistical Analysis

Hooke's standard statistical analysis for EAE studies was applied, according to Table 2 below.

TABLE 2

Statistical analysis performed

| Readout | Statistical analysis |
|---|---|
| EAE incidence | Chi-square test |
| Mean day of EAE onset (sick mice) | 2-tailed Student's t-test |
| Median day of EAE onset (all mice) | Wilcoxon's survival test |
| Average clinical score | Plotted only |
| Average end clinical score | Wilcoxon's non-parametric test |
| Mean maximum score (MMS) | Wilcoxon's non-parametric test |
| Average weight gain/loss | 2-tailed Student's t-test, plotted |
| End weight gain/loss | 2-tailed Student's t-test |

Results and Interpretation

EAE development was evaluated by comparing clinical EAE readouts between the vehicle group and all other groups (Tables 3-6, FIGS. 1 and 2.)

TABLE 3a

Summary of results to Day 28 (end of treatment)

| Group | Treatment | EAE incidence (%) | Median day of onset (all mice) | Mean day of onset +/− SEM (sick mice) | MMS +/− SD | Day 28 score +/− SD | Day 27% body weight +/− SD |
|---|---|---|---|---|---|---|---|
| 1 | Vehicle, i.v., QD | 100.0% | 12.0 | 11.4 +/− 0.5 | 3.68 +/− 0.46 | 3.23 +/− 0.79 | 83.7 +/− 8.3 |
| 2 | arsenic trioxide, 3 mg/kg, i.v., QD | 100.0% | 17.0 | 17.5 +/− 1.1 | 3.41 +/− 0.30 | 2.00 +/− 0.74 | 97.3 +/− 5.1 |

TABLE 3b

Summary of results to Day 35 (end of study)

| Group | Treatment | End score +/- SD | End % body weight +/- SD |
|---|---|---|---|
| 1 | Vehicle, i.v., QD | 3.36 +/- 0.67 | 82.8 +/- 8.1 |
| 2 | arsenic trioxide, 3 mg/kg, i.v., QD | 2.27 +/- 0.75 | 93.2 +/- 6.4 |

Group 1: Vehicle, i.v., OD (Negative Control)

Clinical results for the vehicle group (Group 1, negative control) are shown in Tables 4 and 6, and in FIGS. 1 and 2.

TABLE 4a

Vehicle group (Group 1, negative control) to Day 28 (end of treatment)

| Treatment | EAE incidence (%) | Median day of onset (all mice) | Mean day of onset +/- SEM (sick mice) | MMS +/- SD | Day 28 score +/- SD | Day 27% body weight +/- SD |
|---|---|---|---|---|---|---|
| Vehicle, i.v., QD | 100.0% | 12.0 | 11.4 +/- 0.5 | 3.68 +/- 0.46 | 3.23 +/- 0.79 | 83.7 +/- 8.3 |

TABLE 4b

Vehicle group (Group 1, negative control) to Day 35 (end of study)

| Treatment | End score +/- SD | End % body weight +/- SD |
|---|---|---|
| Vehicle, i.v, QD | 3.36 +/- 0.67 | 82.8 +/- 8.1 |

EAE development in this group was as expected for this model, with maximum scores ranging from 3.5 to 5.0.

All mice in this group lost weight during this study, as expected (Tables 3 and 5, FIG. 2).

Two mice died in this group. One mouse died due to severe EAE while the other death resulted from complications of intravenous dosing (mouse suffocated in the restrainer while being dosed).

Group 2: Arsenic Trioxide, 3 mg/kg, i.v., QD (Test Compound)

Clinical results for this group compared to the vehicle group (Group 1, negative control) are shown in Tables 5 and 6, and in FIGS. 1 and 2.

TABLE 5a

Arsenic trioxide group (Group 2, test compound) compared to the vehicle group (Group 1, negative control) to Day 28 (end of treatment)

| Treatment | EAE incidence (%) | Median day of onset (all mice) | Mean day of onset +/- SEM (sick mice) | MMS +/- SD | Day 28 score +/- SD | Day 27% body weight +/- SD |
|---|---|---|---|---|---|---|
| Vehicle, i.v., QD | 100.0% | 12.0 | 11.4 +/- 0.5 | 3.68 +/- 0.46 | 3.23 +/- 0.79 | 83.7 +/- 8.3 |
| arsenic trioxide 3 mg/kg, i.v., QD | 100.0% | 17.0 | 17.5 +/- 1.1 | 3.41 +/- 0.30 | 2.00 +/- 0.74 | 97.3 +/- 5.1 |

TABLE 5b

Arsenic trioxide group (Group 2, test compound) compared to the vehicle group (Group 1, negative control) to Day 35 (end of study)

| Treatment | End score +/- SD | p value | End % body weight +/- SD | p Value |
|---|---|---|---|---|
| Vehicle, i.v., QD | 3.36 +/- 0.67 | | 82.8 +/- 8.1 | |
| arsenic trioxide 3 mg/kg, i.v., QD | 2.27 +/- 0.75 | 0.0016 | 93.2 +/- 6.4 | 0.0035 |

While 100% of mice in arsenic trioxide group developed EAE (same as in the vehicle group), disease onset was postponed and overall severity was lower in this group compared to the vehicle group (Tables 4 and 5, FIG. 1).

The clinical scores at the end of dosing period (Day 28), as well as at the end of the study, which was 7 days after the treatment was stopped (Day 35), were both significantly lower in the arsenic trioxide treated mice than in the vehicle group.

Consistent with improved clinical scores, arsenic trioxide treated mice had higher body weight compared to the vehicle treated controls (Tables 4 and 5, FIG. 2).

One mouse died in this group. The death did not appear to have resulted from EAE and did not result from complications of i.v. dosing.

Treatment with arsenic trioxide was efficacious at postponing EAE onset and reducing disease severity in this study.

Example 2

The objective of this study was to determine the effects of arsenic trioxide on cytokine production by T lymphocytes from draining lymph nodes and spleen after immunization with $MOG_{35-55}$/CFA.

There were 2 experimental groups with 6 mice/group.

Treatment started on Day −16.

Mice were immunized with $MOG_{35-55}$/CFA on Day 0.

Eleven days after immunization, mice were euthanized, spleens and lymph nodes collected and cell suspensions prepared. Cell suspensions were cultured for 3 days in the presence of multiple concentrations of $MOG_{35-55}$. The culture supernatants were collected at the end of this 3-day culture period. The concentrations of 7 cytokines (IL-2, IL-4, IL-6, IL-10, IL-17A, TNF, and IFN-γ) were determined in the culture supernatants using Th1/Th2/Th17 cytokine bead assay (CBA) kit from Becton Dickinson.

In the spleen cell cultures there was a significant reduction of IL-6 concentration in the arsenic trioxide group at all concentrations of $MOG_{35-55}$ (FIG. 3). This reduction may be large enough to be the mechanism of action for arsenic trioxide in reducing EAE severity. IL-6 is known to be critical in EAE development; this finding may be relevant to arsenic trioxide's mechanism of action in inhibiting EAE development.

The invention claimed is:

1. A method of treating relapsing-remitting multiple sclerosis in a patient, comprising administering from 0.05 to 0.5 mg of arsenic trioxide per kilogram of bodyweight per day to the patient.

2. The method of claim 1, wherein the arsenic trioxide is administered intravenously.

3. The method of claim 1, wherein the arsenic trioxide is administered orally.

4. The method of claim 1, wherein administration of arsenic trioxide to the patient delays new attacks of relapsing-remitting multiple sclerosis in the patient.

5. The method of claim 1, wherein administration of arsenic trioxide to the patient reduces the severity of relapsing-remitting multiple sclerosis in the patient.

* * * * *

UNITED STATES PATENT AND TRADEMARK OFFICE
CERTIFICATE OF CORRECTION

PATENT NO. : 10,716,807 B2
APPLICATION NO. : 15/590254
DATED : July 21, 2020
INVENTOR(S) : Francoise Rieger Page 1 of 1

It is certified that error appears in the above-identified patent and that said Letters Patent is hereby corrected as shown below:

On the Title Page

Item (54) delete "METHOD OF TREATING RELAPSING-REMITTING MULTIPLE SCLEROSIS USING ARSENIC TRIOXIDE" and insert --METHOD OF TREATING MULTIPLE SCLEROSIS USING ARSENIC TRIOXIDE--

Signed and Sealed this
Twenty-ninth Day of September, 2020

Andrei Iancu
*Director of the United States Patent and Trademark Office*